(12) United States Patent
Lin

(10) Patent No.: US 9,375,396 B2
(45) Date of Patent: Jun. 28, 2016

(54) INHALATION-TYPE PHARMACEUTICAL COMPOSITION FOR THE TREATMENT OF HEART DISEASE AND PREPARATION METHOD THEREOF

(71) Applicant: Hsin-Yung Lin, Shanghai (TW)

(72) Inventor: Hsin-Yung Lin, Shanghai (TW)

( * ) Notice: Subject to any disclaimer, the term of this patent is extended or adjusted under 35 U.S.C. 154(b) by 0 days.

(21) Appl. No.: 14/664,491

(22) Filed: Mar. 20, 2015

(65) Prior Publication Data

US 2015/0272868 A1    Oct. 1, 2015

(30) Foreign Application Priority Data

Mar. 25, 2014 (TW) .............................. 103110985 A

(51) Int. Cl.

| | | |
|---|---|---|
| *A61K 31/60* | (2006.01) | |
| *A61K 9/00* | (2006.01) | |
| *A61K 31/137* | (2006.01) | |
| *A61K 31/197* | (2006.01) | |
| *A61K 31/198* | (2006.01) | |
| *A61K 31/277* | (2006.01) | |
| *A61K 31/439* | (2006.01) | |
| *A61K 31/498* | (2006.01) | |
| *A61K 31/13* | (2006.01) | |
| *A61K 31/27* | (2006.01) | |
| *A61K 31/445* | (2006.01) | |
| *A61K 31/55* | (2006.01) | |
| *A61K 47/02* | (2006.01) | |
| *A61K 31/21* | (2006.01) | |
| *A61K 31/34* | (2006.01) | |
| *A61K 31/4365* | (2006.01) | |
| *A61K 31/4406* | (2006.01) | |
| *A61K 31/4422* | (2006.01) | |
| *A61K 31/554* | (2006.01) | |
| *A61K 31/616* | (2006.01) | |
| *A61K 31/192* | (2006.01) | |
| *A61K 31/405* | (2006.01) | |
| *A61K 31/635* | (2006.01) | |
| *A61K 31/165* | (2006.01) | |
| *A61K 31/4152* | (2006.01) | |
| *A61K 31/519* | (2006.01) | |

(52) U.S. Cl.
CPC ................ *A61K 9/0004* (2013.01); *A61K 9/007* (2013.01); *A61K 9/0073* (2013.01); *A61K 31/13* (2013.01); *A61K 31/137* (2013.01); *A61K 31/165* (2013.01); *A61K 31/192* (2013.01); *A61K 31/197* (2013.01); *A61K 31/198* (2013.01); *A61K 31/21* (2013.01); *A61K 31/27* (2013.01); *A61K 31/277* (2013.01); *A61K 31/34* (2013.01); *A61K 31/405* (2013.01); *A61K 31/4152* (2013.01); *A61K 31/439* (2013.01); *A61K 31/4365* (2013.01); *A61K 31/445* (2013.01); *A61K 31/4406* (2013.01); *A61K 31/4422* (2013.01); *A61K 31/498* (2013.01); *A61K 31/519* (2013.01); *A61K 31/55* (2013.01); *A61K 31/554* (2013.01); *A61K 31/616* (2013.01); *A61K 31/635* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 2010/0030091 A1* | 2/2010 | Fine | ........................ A61K 31/04 600/508 |
| 2012/0309809 A1 | 12/2012 | Green et al. | |

FOREIGN PATENT DOCUMENTS

DE          19734279 A1 *    2/1999    ............. A61K 33/00

OTHER PUBLICATIONS

Ohta, S. Curr Pharm Design 2011 vol. 17 pp. 2241-2252.*
Eschwey, M et al DE 19734279 English translation.*
Contractor, A et al, J Pharmaceut. Sci 1974 vol. 63 pp. 907-911.*

* cited by examiner

*Primary Examiner* — Heidi Reese
(74) *Attorney, Agent, or Firm* — Foster Pepper PLLC; Richard A. Koske; P. G. Scott Born

(57) ABSTRACT

The present invention provides an inhalation-type pharmaceutical composition for heart disease and preparation method thereof, comprising a first gas and an atomized medicine. The first gas comprises hydrogen. The gas volume concentration of hydrogen in the inhalation-type pharmaceutical composition is between 2 to 96%. The atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof. The inhalation-type pharmaceutical composition of the present invention can remove harmful radicals in the body of the patient through the use of hydrogen while also increases the absorption effect of the medicine for the patient by using an atomized medicine. At the same time, because the use of the small amount of the vaporized pharmaceutical liquid can indirectly reduce the side effects on the user.

17 Claims, 4 Drawing Sheets

(1)

INHALATION-TYPE PHARMACEUTICAL COMPOSITION FOR THE TREATMENT OF HEART DISEASE AND PREPARATION METHOD THEREOF

PRIORITY CLAIM

This application claims the benefit of the filing date of Taiwan Patent Application No. 103110985, filed Mar. 25, 2014, entitled "INHALATION-TYPE PHARMACEUTICAL COMPOSITION FOR THE TREATMENT OF HEART DISEASE AND PREPARATION METHOD THEREOF," and the contents of which are hereby incorporated by reference in their entirety.

FIELD OF THE INVENTION

The present invention relates to an inhalation-type pharmaceutical composition and the preparation method thereof, more particularly, to the inhalation-type pharmaceutical composition used for the treatment of heart disease and the preparation method thereof.

BACKGROUND

Nowaday, with the continuous improvement of people's living standards, the living and eating habits are gradually westernized. Therefore, the number of patients of heart disease is substantial increasing, and the heart disease is located in one of the top ten causes of death in people. At the same time, the average age of onset of heart disease has gradually decreased, so the heart disease has become a serious threat to human health.

Heart disease is a general term for heart disease, including congenital heart disease, rheumatic heart disease, hypertensive heart disease, and coronary heart disease. The main cause of heart disease is stenosis, sclerosis or occlusion of coronary artery, where cardiac hypoxia is caused by insufficient blood supply to the heart, called coronary artery disease, CAD. The coronary artery diseases comprise coronary arteriosclerosis, coronary atherosclerosis, coronary heart disease, ischemic cardiac disease, angina pectoris, and myocardial infarction.

In the prior art, the medications for the treatment of heart disease include Anti-platelet aggregation medicinal, such as acetylsalicylic acid, clopidogrel; β-adrenoceptor blockers, such as propranolol, atenolol, nadolol, carvedilol; calcium channel blocker, such as nifedipine, diltiazem, verapamil; nitrate drugs, such as isosorbide dinitrate, nicorandil; and nitroglycerin, NTG. However, those aforementioned pharmaceuticals usually have some side effects, such as the symptoms of headache, rapid heartbeat, and even some patients will appear in a coma after taking nitroglycerin, such that those aforementioned pharmaceuticals are not suitable for long-term use.

Therefore, the current treatment for heart disease lacks a medicine combined with the curative effect for heart disease and reducing side effects to patients.

SUMMARY OF THE INVENTION

Therefore, the present invention provides an inhalation-type pharmaceutical composition for the treatment of heart disease, which comprises a first gas and an atomized medicine. The first gas comprises hydrogen, where the gas volume concentration of the hydrogen in the inhalation-type pharmaceutical composition is between 2 to 96%. The atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof.

According to the preparation method for the inhalation-type pharmaceutical composition for the treatment of heart disease provided by one embodiment of the present invention, the first gas is a gas mixture of hydrogen and oxygen generated from electrolyzing water, where the volume ratio of hydrogen to oxygen is 2:1. In the embodiment, the gas volume concentration of hydrogen in the inhalation-type pharmaceutical composition is between 2 to 66.66%. Furthermore, the inhalation-type pharmaceutical composition of the present invention further comprises a second gas. The second gas is used to reduce the gas volume concentration of hydrogen in the inhalation-type pharmaceutical composition, wherein the second gas is a gas selected from a group comprising air, water vapor, inert gas, oxygen or any combination thereof. In the present embodiment, the gas volume concentration of hydrogen in the inhalation-type pharmaceutical composition can be between 4.7 to 66.66%, but is not limited to this range.

According to the inhalation-type pharmaceutical composition for the treatment of heart disease provided by another embodiment of the present invention, the gas volume concentration of hydrogen in the inhalation-type pharmaceutical composition is between 60 to 66.66%. In addition, the inhalation-type pharmaceutical composition for the treatment of heart disease provided by another embodiment of the present invention, the gas volume concentration of hydrogen in the inhalation-type pharmaceutical composition is larger than 66.66%.

Furthermore the invention further provides a preparation method for the inhalation-type pharmaceutical composition for the treatment of heart disease, and comprises the following steps:

(S1) preparing a first gas, wherein the first gas comprises hydrogen;

(S2) atomizing a medicinal liquid in order to generate an atomized medicine, wherein the atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof; and (S3) mixing the first gas and the atomized medicine in order to generate the inhalation-type pharmaceutical composition, wherein the gas volume concentration of hydrogen in the inhalation-type pharmaceutical composition is between 2 to 96%.

According to the preparation method for the inhalation-type pharmaceutical composition for the treatment of heart disease provided by one embodiment of the present invention, the first gas is generated by electrolyzing water in step (S1) of the present invention. The first gas comprises a gas mixture of hydrogen and oxygen, where the volume ratio of hydrogen to oxygen is 2:1.

According to the preparation method for the inhalation-type pharmaceutical composition for the treatment of heart disease provided by another embodiment of the present invention, the method of the present invention further comprises the following steps:

(S21) preparing a first gas, wherein the first gas comprises hydrogen;

(S22) atomizing a medicinal liquid to generate an atomized medicine, wherein the atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof;

(S23) preparing a second gas; and (S24) mixing the first gas, the second gas, and the atomized medicine in order to generate the inhalation-type pharmaceutical composition. In the embodiment, the gas volume concentration of hydrogen in the inhalation-type pharmaceutical composition for the treatment of heart disease can be reduced by adding the second gas.

Furthermore, according to the preparation method for the inhalation-type pharmaceutical composition for the treatment of heart disease provided by another embodiment of the present invention, the gas volume concentration of hydrogen in the inhalation-type pharmaceutical composition is generally between 60%~66.61%. And according to the preparation method for the inhalation-type pharmaceutical composition for the treatment of heart disease provided by another embodiment of the present invention, the gas volume concentration of hydrogen in the inhalation-type pharmaceutical composition generally is larger than 66.66%.

Compared to conventional technology, the present invention provides an inhalation-type pharmaceutical composition for the treatment of heart disease and the preparation method thereof. The inhalation-type pharmaceutical composition of the present invention can provide the convenience of taking medicine and removing harmful radicals in the body of the patient through the use of hydrogen while also increases the absorption effect of the medicine for the patient by using an atomized medicine. Therefore, the present invention can provide a treatment for heart disease that combines the convenience of taking the medicine while also having better curative effects on the user.

DETAILED DESCRIPTION

Figure 1:
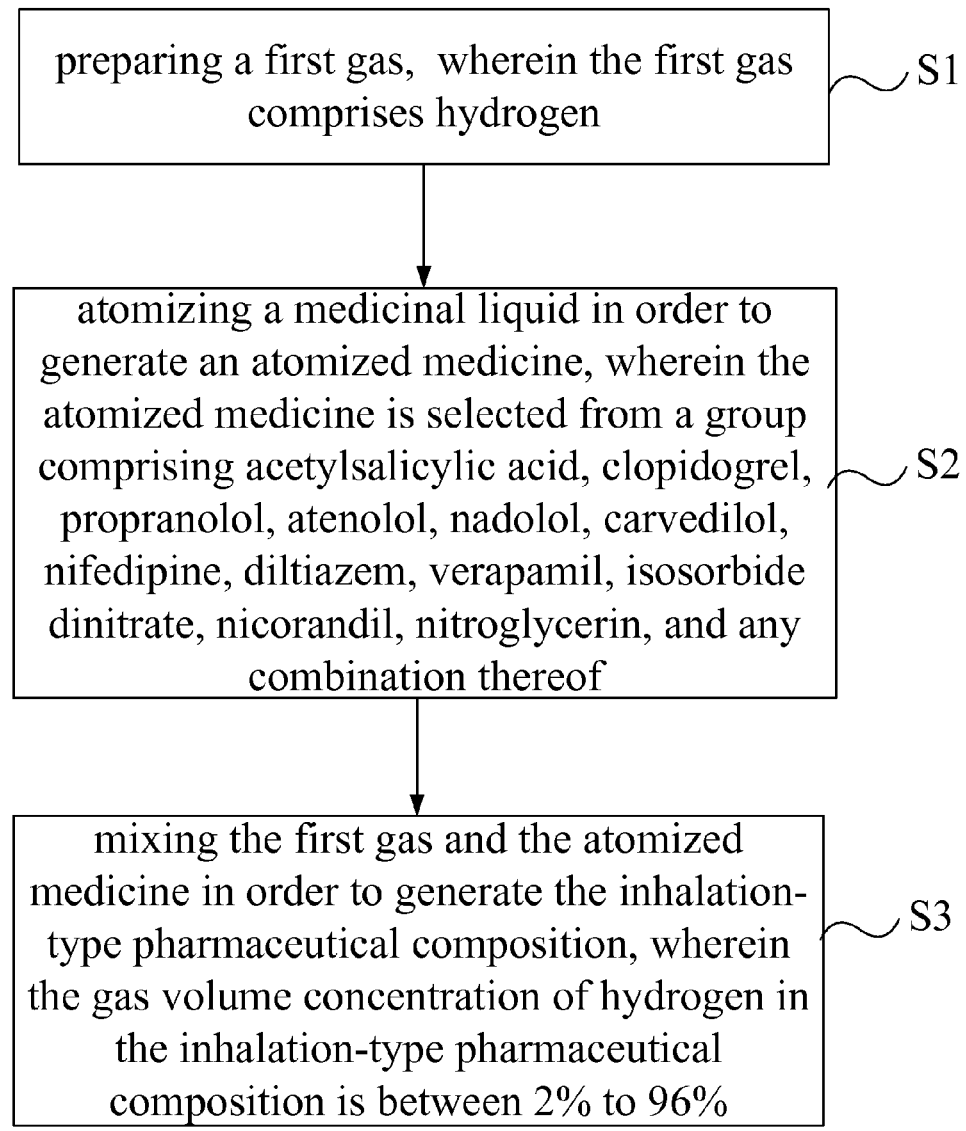
FIG. 1 is a method flowchart illustrating a preparation method for an inhalation-type pharmaceutical composition for the treatment of heart disease according to one embodiment of the present invention.

In order to allow the advantages, spirit and features of the present invention to be more easily and clearly understood, the embodiments and appended drawings thereof are discussed in the following. However, the present invention is not limited to the embodiments and appended drawings.

The present invention provides an inhalation-type pharmaceutical composition for the treatment of heart disease, which comprises a first gas and an atomized medicine. The first gas comprises hydrogen. The gas volume concentration of hydrogen in the inhalation-type pharmaceutical composition is between 2 to 96%. The atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof.

In one embodiment of the present invention, the first gas further comprises an oxygen and is a gas mixture of hydrogen and oxygen generated from electrolyzing water, where the volume ratio of hydrogen to oxygen is 2:1. The atomized medicine is generated by atomizing or vaporizing a medicinal liquid, wherein the medicinal liquid is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof. The above medicine for the treatment of heart disease is well known to those skilled in the art, and hence will not be described in further detail. In the present embodiment, the gas volume concentration of hydrogen in the inhalation-type pharmaceutical composition is between 2 to 66.66%.

The inhalation-type pharmaceutical composition of the present invention further comprises a second gas. The second gas is used to reduce the gas volume concentration of hydrogen in the inhalation-type pharmaceutical composition, wherein the second gas is a gas selected from a group comprising air, water vapor, inert gas, oxygen or any combination thereof. In the present embodiment, the gas volume concentration of hydrogen in the inhalation-type pharmaceutical composition can be between 4.7 to 66.66%, but is not limited to this range.

In another embodiment of the present invention, the inhalation-type pharmaceutical composition is made by mixing the first gas and the atomized medicine generated by atomizing a 40 c.c. medicinal liquid, where the gas volume concentration of hydrogen in the inhalation-type pharmaceutical composition is between 60 to 66.66%. In another embodiment of the present invention, the required hydrogen can be provided by using a hydrogen bottle. Then, the hydrogen provided by the hydrogen bottle is mixed with the atomized medicine, where at this time the gas volume concentration of hydrogen in the inhalation-type pharmaceutical composition is larger than 66.66%, for example between 67 to 96%. In another embodiment of the present invention, the hydrogen can also be directly collected from the hydrogen generated in the electrolyzed water. The hydrogen is then collected from the hydrogen generated in the electrolyzed water, not the gas mixture of hydrogen and oxygen, and is directly mixed with the atomized medicine, where at this time the gas volume concentration of hydrogen in the inhalation-type pharmaceutical composition will also be larger than 66.66%.

Please refer to FIG. 1. FIG. 1 is a method flowchart illustrating a preparation method for an inhalation-type pharmaceutical composition for the treatment of heart disease according to one embodiment of the present invention. As shown in FIG. 1, the preparation method for the inhalation-type pharmaceutical composition of the present invention comprises the following steps:

(S1) preparing a first gas, wherein the first gas comprises hydrogen;

(S2) atomizing a medicinal liquid in order to generate an atomized medicine, wherein the atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof; and (S3) mixing the first gas and the atomized medicine in order to generate the inhalation-type pharmaceutical composition, wherein the gas volume concentration of hydrogen in the inhalation-type pharmaceutical composition is between 2 to 96%.

According to the preparation method for the inhalation-type pharmaceutical composition for the treatment of heart disease provided by one embodiment of the present invention, the first gas is generated by electrolyzing water in step (S1) of the present invention. The first gas comprises a gas mixture of hydrogen and oxygen, where the volume ratio of hydrogen to oxygen is 2:1. In the embodiment, the gas volume concentration of hydrogen in the inhalation-type pharmaceutical composition is between 2 to 66.66%, but is not limited to this range.

Figure 2:
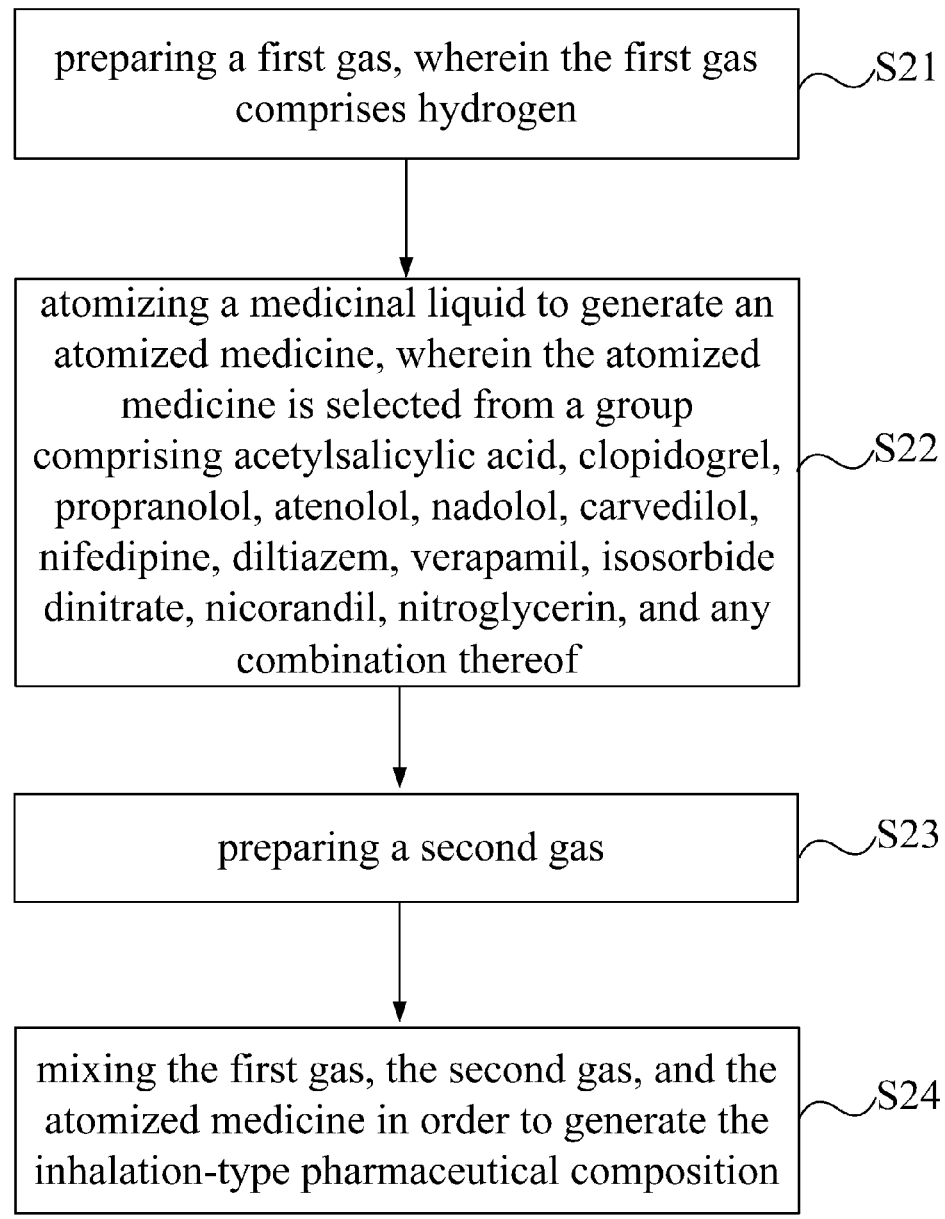
FIG. 2 is a method flowchart illustrating a preparation method for an inhalation-type pharmaceutical composition for the treatment of heart disease according to another embodiment of the present invention.

Please refer to FIG. 2. FIG. 2 is a method flowchart illustrating a preparation method for an inhalation-type pharmaceutical composition for the treatment of heart disease according to another embodiment of the present invention. As shown in FIG. 2, another preparation method for the inhalation-type pharmaceutical composition of the present invention comprises the following steps:

(S21) preparing a first gas, wherein the first gas comprises hydrogen;

(S22) atomizing a medicinal liquid in order to generate an atomized medicine, wherein the atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof;

(S23) preparing a second gas; and (S24) mixing the first gas, the second gas, and the atomized medicine in order to generate the inhalation-type pharmaceutical composition.

According to the preparation method for the inhalation-type pharmaceutical composition for the treatment of heart disease provided by one embodiment of the present invention, the first gas is generated by electrolyzing water in step (S21) of the present invention. The first gas comprises a gas mixture of hydrogen and oxygen, where the volume ratio of hydrogen to oxygen is 2:1. Furthermore, the gas volume concentration of hydrogen in the inhalation-type pharmaceutical composition can be reduced by adding the second gas. In the present embodiment, the gas volume concentration of hydrogen in the inhalation-type pharmaceutical composition is between 4.7 to 66.66%, but is not limited to this range.

In another embodiment of the present invention, the required hydrogen can also be provided by using a hydrogen bottle. The hydrogen provided by the hydrogen bottle is then mixed with the atomized medicine, where at this time the gas volume concentration of hydrogen in the inhalation-type pharmaceutical composition is larger than 66.66%, for example between 67 to 96%. When a user inhales gas with higher gas volume concentration of hydrogen, such as the gas volume concentration of hydrogen being higher than 96%, namely gas inhaled by the user has lower gas volume concentration of oxygen, which would result in lack of oxygen to the user's body. Therefore, it is imperative that the invention controls the volume concentration of hydrogen to not be higher than 96%, for example having the gas volume concentration of hydrogen in the inhalation-type pharmaceutical composition to be between 67 to 90%. In another embodiment of the present invention, hydrogen can also be directly collected from the hydrogen generated in the electrolyzed water. The hydrogen collected from the hydrogen generated in the electrolyzed water, not a gas mixture of hydrogen and oxygen, is directly mixed with the atomized medicine, where at this time the gas volume concentration of hydrogen in the inhalation-type pharmaceutical composition will also be larger than 66.66%.

Figure 3:
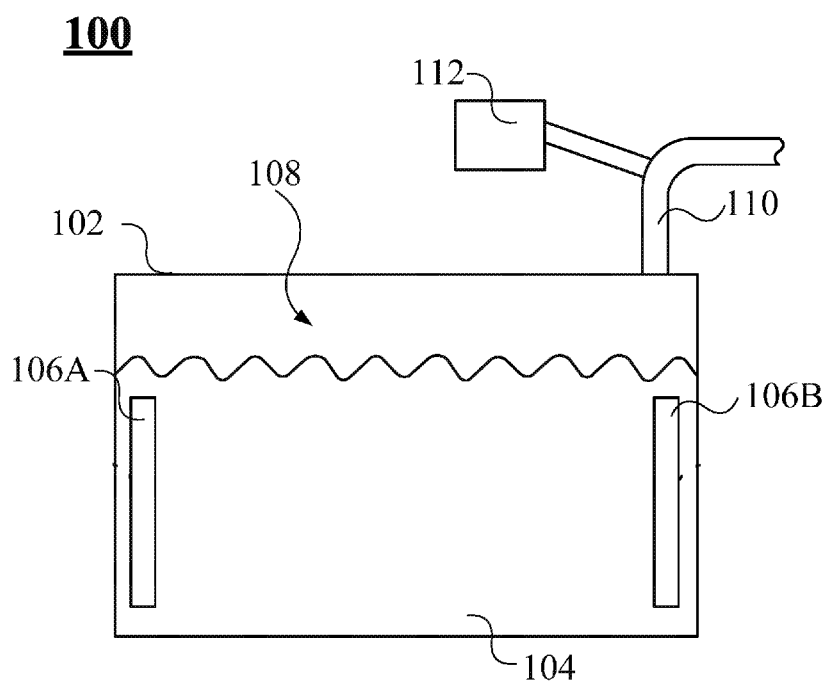
FIG. 3 is a schematic diagram of an electrolysis device illustrating step (S1) in the preparation method for an inhalation-type pharmaceutical composition for the treatment of heart disease according to one embodiment of the present invention.

Please refer to FIG. 3. FIG. 3 is a schematic diagram of an electrolysis device illustrating step (S1) in the preparation method for an inhalation-type pharmaceutical composition for the treatment of heart disease according to one embodiment of the present invention. In the present embodiment, the first gas comprising the gas mixture of hydrogen and oxygen can be generated by electrolyzing water, wherein an electrolysis device 100 comprises an electrolysis tank 102, electrolytic water 104, two electrodes 106A and 106B, and a power supply.

Firstly, the electrolysis tank 102 is used to accommodate the electrolytic water 104, wherein the main ingredient of the electrolytic water 104 is pure water, but is not limited thereof. In practical application, electrolytes such as sodium hydroxide, calcium carbonate and sodium chloride can be added into the electrolyzed water 104 as needed. Then, the electrolysis tank 102 comprises two electrodes 106A and 106B, wherein the two electrodes 106A and 106B respectively represent a cathode electrode and an anode electrode. The two electrodes 106A and 106B are coupled to a power supply (not shown) in order to provide the required power to electrolyze the water. In one embodiment of the present invention, the polarity of the two electrodes 106A and 106B are fixed, for example, the electrode 106A is the cathode and the electrode 106B is the anode. In another embodiment of the present invention, the polarity of the two electrodes 106A and 106B can be alternated. For example, at a point in time, the electrode 106A is the cathode and the electrode 106B is the anode, but after a predetermined time, the electrode 106A changes into the anode and the electrode 106B changes into the cathode.

After the two electrodes 106A and 106B are powered, the water 104 in the electrolysis tank 102 will begin to be electrolyzed in order to generate hydrogen and oxygen. Hydrogen is generated on the cathode and oxygen is generated on the anode, and both hydrogen and oxygen are released to the upper part of the electrolysis tank 102 in order to form a first gas 108. The first gas 108 is outputted from a first gas line 110 of the electrolysis tank 102 to be used, but is not limited thereof. In another embodiment of the present invention, hydrogen from the cathode and oxygen from the anode are outputted to the electrolysis tank 102 through a gas pipe and then mixed to form the first gas 108.

Figure 4:
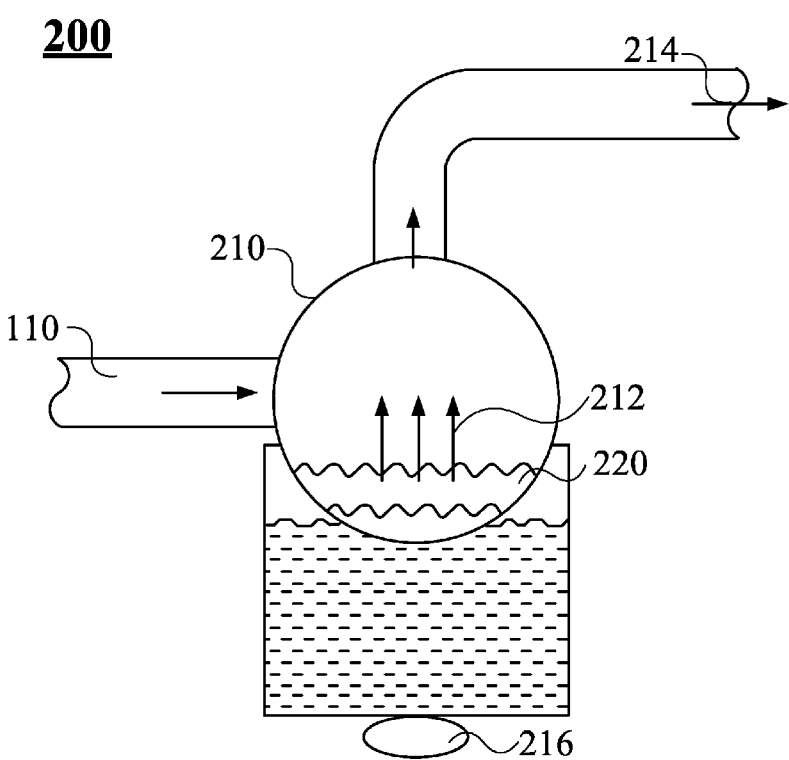
FIG. 4 is a schematic diagram of a gas mixing system illustrating step (S2) and (S3) in the preparation method of the inhalation-type pharmaceutical composition for the treatment of heart disease according to one embodiment of the present invention.

Hydrogen and oxygen are generated from electrolyzing the water 104, where the volume ratio of hydrogen to oxygen is 2:1. In one embodiment of the present invention, the invention can further add a second gas 112 to the inhalation-type pharmaceutical composition to reduce the gas volume concentration of hydrogen in the inhalation-type pharmaceutical composition. For example, the gas volume concentration of hydrogen in the inhalation-type pharmaceutical composition can be controlled to be between 4.7 to 66.66%. The second gas is a gas selected from a group comprising air, water vapor, inert gas, oxygen or any combination thereof Please refer to FIG. 4. FIG. 4 is a schematic diagram of a gas mixing system illustrating step (S2) and (S3) in the preparation method of an inhalation-type pharmaceutical composition for the treatment of heart disease according to one embodiment of the present invention. In step (S2) and (S3) of the preparation method, a medicinal liquid 220 can be atomized by a gas mixing system 200, and then the atomized medicinal liquid 220 can be mixed with the first gas 108 in order to generate an inhalation-type pharmaceutical composition 214.

The gas mixing system 200 comprises an atomized/volatile gas mixing tank 210. The atomized/volatile gas mixing tank 210 is coupled to the electrolysis device 100 by the first gas line 110, as shown in FIG. 3, which is used to accept the first gas 108 to mix an atomized medicine 212 in order to generate the inhalation-type pharmaceutical composition 214. The atomized/volatile gas generator 210 further comprises an oscillator 216, such as an ultrasonic oscillator. The oscillator 216 is adapted to atomize the medicinal liquid 220 in the atomized/volatile gas generator 210 in order to generate the atomized medicine 212. The medicinal liquid 220 can be a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof. The above medicine for the treatment of heart disease is well known to those skilled in the art, and hence will not be described in further detail.

In another embodiment of the present invention, the atomized/volatile gas generator 210 can accommodate between 40 c.c. and 100 c.c of medicinal liquid, which can be completely atomized within 60 min using the atomized/volatile gas generator 210. Therefore, the gas yield of the atomized medicine can be between about 0.67 cc/min to about 1.67 cc/min, and the gas yield controlled by the electrolysis tank 102 can be between about 2,000 cc/min to about 3,000 cc/min, wherein the gas generated from the electrolysis tank only has the gas mixture of hydrogen and oxygen (the volume ratio of hydrogen to oxygen is about 2:1), and thus the gas volume concentration of hydrogen in the inhalation-type pharmaceutical composition is between 66.61 and 66.65%. The heat is generated from the electrolysis tank when the electrolytic tank is conducted to electrolyze. The water in the electrolysis tank will then be evaporated by the heat generated from the electrolysis tank. Then the gas generated from the electrolysis tank not only has the gas mixture of hydrogen and oxygen but also has a small amount of water vapor, therefore the gas volume concentration of hydrogen in the inhalation-type pharmaceutical composition will be lower than 66.61%, for example the gas volume concentration of hydrogen in the inhalation-type pharmaceutical composition can be between 60 and 66.61%. Evidently, the small amount of water vapor can be reduced through cooling. Therefore, the inhalation-type pharmaceutical composition for the treatment of heart disease can be made by mixing the gas mixture of hydrogen and oxygen with the atomized medicine. The gas volume concentration of hydrogen in the inhalation-type pharmaceutical composition is generally between 60%~66.61%.

In another embodiment of the present invention, the composition ratio of the first gas and the atomized medicine in the inhalation-type pharmaceutical composition separately are 35.33~99.99% and 0.01~64.67%, which are calculated according to the concentration percentage of the gas, but are not limited thereof. In practical application, the composition ratio of the first gas and the atomized medicine can be adjusted according to the patient's situation and is also administered daily through inhalation at least one to three times, where each session may be in the range of 30 to 60 minutes.

In another embodiment of the present invention, the composition ratio of the first gas, the atomized medicine and the second gas in the inhalation-type pharmaceutical composition separately are 33~97%, 0.01~64%, and 2~66%, which are calculated according to the concentration percentage of the gas, but are not limited thereof. In practical application, the composition ratio of the first gas, the atomized medicine and the second gas can be adjusted according to the patient's situation and is also administered daily through inhalation at least one to three times, where each session may be in the range of 30 to 60 minutes.

According to the above embodiments of the present invention, the inhalation-type pharmaceutical composition of the present invention comprises hydrogen and the atomized medicine in order to form the inhalation-type pharmaceutical composition that is to be inhaled by a user (not shown). Studies have found that there is an instable oxygen species (O+), also known as free radicals, in the human body. The free radicals are usually created due to diseases, diet, environment and one's lifestyle, where the free radicals can be excreted in the form of water by reacting with the inhaled hydrogen. Using this method, the amount of free radicals in the human body can be reduced, thereby restoring the body condition from an acidic state to an alkaline state, which can achieve an anti-oxidation, anti-aging and beauty health effect, and even eliminating chronic diseases. In addition, according to clinical studies, the atomized medicinal liquid is 1-5 micro meters and is more easily absorbed by the human body than its non-atomized counterpart. That is to say, compared with its non-atomized counterpart, the atomized medicine can achieve the same therapeutic effect with a much lower dosage. Furthermore, the drug's side effects can be reduced due to the lower dosage of administered atomized medicine. The medicinal liquid may be the liquid mixture that is oral medicine dissolved in the water. Therefore, the inhalation-type pharmaceutical composition having hydrogen and the atomized medicine may provide an excellent therapeutic effect.

Compared to conventional technology, the present invention provides an inhalation-type pharmaceutical composition for the treatment of heart disease and the preparation method thereof. The inhalation-type pharmaceutical composition of the present invention can provide the convenience of taking medicine and removing harmful radicals in the body of the patient through the use of hydrogen while also increases the absorption effect of the medicine for the patient by using an atomized medicine. At the same time, because the use of the small amount of the vaporized pharmaceutical liquid can indirectly reduce the side effects on the user.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the meets and bounds of the appended claims.

The invention claimed is:

1. An inhalation-type pharmaceutical composition for the treatment of heart disease, comprising a first gas and an atomized medicine, wherein the first gas comprises hydrogen and oxygen, the gas volume concentration of hydrogen in the inhalation-type pharmaceutical composition is between 2 to 96%, the atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof, wherein the first gas is a gas mixture of hydrogen and oxygen generated from electrolyzing water, and the volume ratio of hydrogen to oxygen is 2:1.

2. The inhalation-type pharmaceutical composition for the treatment of heart disease of claim 1, further comprising a second gas for reducing the gas volume concentration of hydrogen in the inhalation-type pharmaceutical composition, wherein the second gas is a gas selected from a group comprising air, water vapor, inert gas, oxygen or any combination thereof.

3. The inhalation-type pharmaceutical composition for the treatment of heart disease of claim 1, wherein the gas volume concentration of hydrogen in the inhalation-type pharmaceutical composition is between 2 to 66.66%.

4. The inhalation-type pharmaceutical composition for the treatment of heart disease of claim 1, wherein the gas volume concentration of hydrogen in the inhalation-type pharmaceutical composition is between 4.7 to 66.66%.

5. The inhalation-type pharmaceutical composition for the treatment of heart disease of claim 1, wherein the gas volume concentration of hydrogen in the inhalation-type pharmaceutical composition is between 60 to 66.66%.

6. The inhalation-type pharmaceutical composition for the treatment of heart disease of claim 1, wherein the gas volume concentration of hydrogen in the inhalation-type pharmaceutical composition is larger than 66.66%.

7. The inhalation-type pharmaceutical composition for the treatment of heart disease of claim 1, wherein the atomized medicine is generated by atomizing or vaporizing a medicinal liquid.

8. The inhalation-type pharmaceutical composition for the treatment of heart disease of claim 7, wherein the medicinal liquid is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof.

9. A preparation method for an inhalation-type pharmaceutical composition for the treatment of heart disease, comprising the following steps:
(S1) preparing a first gas, wherein the first gas is generated by electrolyzing water, the first gas comprises a gas mixture of hydrogen and oxygen, and the volume ratio of hydrogen to oxygen is 2:1;
(S2) atomizing a medicinal liquid in order to generate an atomized medicine, wherein the atomized medicine is selected from a group comprising acetylsalicylic acid, clopidogrel, propranolol, atenolol, nadolol, carvedilol, nifedipine, diltiazem, verapamil, isosorbide dinitrate, nicorandil, nitroglycerin, and any combination thereof; and
(S3) mixing the first gas and the atomized medicine in order to generate the inhalation-type pharmaceutical composition, wherein the gas volume concentration of hydrogen in the inhalation-type pharmaceutical composition is between 2 to 96%.

10. The preparation method for the inhalation-type pharmaceutical composition for the treatment of heart disease of claim 9, further comprising the following step after step (S2):
(S23) preparing a second gas.

11. The preparation method for the inhalation-type pharmaceutical composition for the treatment of heart disease of claim 10, wherein in step (S3), the inhalation-type pharmaceutical composition is generated from mixing the first gas, the second gas, and the atomized medicine.

12. The preparation method for the inhalation-type pharmaceutical composition for the treatment of heart disease of claim 10, wherein the second gas is used for reducing the gas volume concentration of hydrogen in the inhalation-type pharmaceutical composition.

13. The preparation method for the inhalation-type pharmaceutical composition for the treatment of heart disease of claim 10, wherein the second gas is a gas selected from a group comprising air, water vapor, inert gas, oxygen or any combination thereof.

14. The preparation method for the inhalation-type pharmaceutical composition for the treatment of heart disease of claim 9, wherein the gas volume concentration of hydrogen in the inhalation-type pharmaceutical composition is between 2 to 66.66%.

15. The preparation method for the inhalation-type pharmaceutical composition for the treatment of heart disease of claim 9, wherein the gas volume concentration of hydrogen in the inhalation-type pharmaceutical composition is between 4.7 to 66.66%.

16. The preparation method for the inhalation-type pharmaceutical composition for the treatment of heart disease of claim 9, wherein the gas volume concentration of hydrogen in the inhalation-type pharmaceutical composition is between 60 to 66.66%.

17. The preparation method for the inhalation-type pharmaceutical composition for the treatment of heart disease of claim 9, wherein the gas volume concentration of hydrogen in the inhalation-type pharmaceutical composition is larger than 66.66%.

* * * * *